(12) United States Patent
Nagatomo et al.

(10) Patent No.: US 7,731,902 B2
(45) Date of Patent: Jun. 8, 2010

(54) PHOTONIC CRYSTAL AND WAVEGUIDE SENSOR DEVICE

(75) Inventors: Yasuhiro Nagatomo, Kawasaki (JP); Mitsuro Sugita, Ohta-ku (JP); Mamoru Uchida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1006 days.

(21) Appl. No.: 11/276,255

(22) Filed: Feb. 21, 2006

(65) Prior Publication Data

US 2006/0216200 A1    Sep. 28, 2006

(30) Foreign Application Priority Data

Feb. 25, 2005   (JP)   .............. 2005-051998

(51) Int. Cl.
*G01N 21/63*   (2006.01)
*G01N 21/01*   (2006.01)
*G01J 3/00*    (2006.01)

(52) U.S. Cl. .................. 422/82.11; 356/244; 356/300; 385/12; 422/82; 422/82.05

(58) Field of Classification Search .............. 422/82.05, 422/82.11, 82, 22; 385/12; 356/244, 300
See application file for complete search history.

(56) References Cited

U.S. PATENT DOCUMENTS

| | | | | |
|---|---|---|---|---|
| 3,697,185 A | * | 10/1972 | Kassel et al. ................ | 356/410 |
| 4,344,078 A | * | 8/1982 | Houston .................... | 347/81 |
| 4,669,878 A | * | 6/1987 | Meier ....................... | 356/319 |
| 5,071,248 A | * | 12/1991 | Tiefenthaler et al. ........ | 356/128 |
| 5,210,590 A | * | 5/1993 | Landa et al. ................. | 356/319 |
| 5,297,224 A | * | 3/1994 | Shaw .......................... | 385/12 |
| 5,345,522 A | * | 9/1994 | Vali et al. ..................... | 385/24 |
| 5,485,277 A | * | 1/1996 | Foster ........................ | 356/445 |
| 5,699,373 A | | 12/1997 | Uchida et al. | |
| 5,715,173 A | * | 2/1998 | Nakajima et al. ........... | 700/266 |
| 5,930,031 A | * | 7/1999 | Zhou et al. .................. | 359/344 |
| 6,081,633 A | * | 6/2000 | Kersey et al. ................ | 385/12 |
| 6,084,233 A | * | 7/2000 | Hodgson et al. ....... | 250/227.14 |

(Continued)

FOREIGN PATENT DOCUMENTS

JP    2003-75447 A    3/2003

OTHER PUBLICATIONS

Miguez, H. et al, Langmuir 2003, 19, 3479-3485.*

(Continued)

*Primary Examiner*—Arlen Soderquist
(74) *Attorney, Agent, or Firm*—Fitzpatrick, Cella, Harper & Scinto (57) ABSTRACT

The present invention provides a sensor device for detecting a substance contained in a fluid comprising a first photonic crystal region, a second photonic crystal region, a first channel which is connected to the first photonic crystal region, and passes the fluid containing the substance therein, a second channel which is connected to the second photonic crystal region, and passes a fluid for reference therein, an optical waveguide which is connected to the first photonic crystal region and the second photonic crystal region, and guides light, and a detecting section for detecting a difference between a light which has passed through the optical waveguide and the first photonic crystal region and a light which has passed through the optical waveguide and the second photonic crystal region.

4 Claims, 6 Drawing Sheets

U.S. PATENT DOCUMENTS

| | | | |
|---|---|---|---|
| 6,198,869 B1 * | 3/2001 | Kraus et al. | 385/129 |
| 6,721,053 B1 * | 4/2004 | Maseeh | 356/436 |
| 6,726,881 B2 | 4/2004 | Shinoki et al. | |
| 6,970,247 B2 * | 11/2005 | Yankielun | 356/436 |
| 6,977,820 B2 | 12/2005 | Uchida | |
| 7,189,362 B2 * | 3/2007 | Nordin et al. | 422/82.11 |
| 2002/0031838 A1 * | 3/2002 | Meinhart et al. | 436/514 |
| 2002/0110839 A1 * | 8/2002 | Bach et al. | 435/7.9 |
| 2003/0108294 A1 * | 6/2003 | Zheng | 385/39 |
| 2003/0128364 A1 * | 7/2003 | Dickopf et al. | 356/445 |
| 2004/0118189 A1 * | 6/2004 | Karp et al. | 73/61.52 |
| 2005/0018949 A1 * | 1/2005 | Yan | 385/14 |
| 2005/0200942 A1 * | 9/2005 | Grot et al. | 359/321 |
| 2005/0201660 A1 * | 9/2005 | Grot et al. | 385/12 |
| 2006/0056756 A1 | 3/2006 | Uchida | |
| 2006/0067605 A1 * | 3/2006 | Mirkarimi et al. | 385/12 |
| 2006/0106557 A1 * | 5/2006 | Fontaine et al. | 702/87 |
| 2006/0188398 A1 | 8/2006 | Yano et al. | |

OTHER PUBLICATIONS

Applied Physics Letters (Photonic crystal laser sources for chemical detection), vol. 82, No. 26, Jun. 30, pp. 4648-4650 (2003).

* cited by examiner

PHOTONIC CRYSTAL AND WAVEGUIDE SENSOR DEVICE

BACKGROUND OF THE INVENTION

1. Field of the Invention

The present invention relates to a sensor device used for measuring the refractive index of a fluid flowing in a channel and detecting a target substance in the fluid.

2. Related Background Art

In recent years, a high-performance biochip and a high-performance sensor using a new technology for analyzing/detecting an organism have been expected as means of realizing a brief home medical examination and proteomics for elucidating the structure and function of protein. For instance, a sensor device using a DNA chip, a DNA microarray, surface plasmon resonance, a multiplex internal reflection method and a photonic crystal has been suggested, researched and developed.

A method for analyzing/detecting an organism using a DNA-microarray makes use of the molecular recognition capacity of a DNA molecule. The DNA microarray has several types of DNA or oligonucleotide arranged on a small carrier such as glass at high density. When a gene is analyzed with the organism-analyzing method, the DNA to be arranged there is cDNA of genetic origin, or the like. As an example, a case of analyzing the gene will be described below. The gene expression is analyzed by the steps of labeling a mRNA or cDNA sample extracted from a specimen with a fluorescent dye; immersing the DNA microarray into a solution containing the labeled sample to make each spot in the DNA microarray emit different fluorescent colors depending on the hybridized ways of a DNA probe with the sample; and analyzing the intensity of the fluorescent signal.

Particularly, a DNA microarray having DNA integrated on the surface of a silicon substrate with the use of photolithography has been called a DNA chip. In a gene analysis using the DNA chip, several types of oligonucleotide are artificially synthesized each in separate micro areas on the surface of a substrate such as glass and a semiconductor. The procedure of the analysis employs hybridization and fluorescent labeling, as in the case of using the DNA microarray. The DNA chip is commercially available under the registered trademark of Gene Chip by Affymetrix Corporation in the United States. Recently, even the DNA microarray prepared by using means such as an ink jet technique other than lithography has been called the DNA chip.

One problem of a procedure using a DNA microarray is to need fluorescent labeling. When the sample is labeled, a procedure of labeling the sample may deteriorate the specificity in DNA hybridization or cause variation in labeling due to variation in the procedure, which may deteriorate the quantitativity of the analysis. Accordingly, the analysis method has not yet been practically used in the true sense in a medical scene. On the other hand, an organism-analyzing/detecting method which does not need fluorescent labeling has been also developed actively. Examples of them are the methods of using the above described surface plasmon resonance, multiple internal reflection method and photonic crystal. The methods all use light for detection.

Generally, a sensor device using light for detection often employs a structure using an interference effect of light. A method for composing the interference sensor device includes a ring type, a Michelson type, a Fabry-Perot type and a Mach-Zehnder type, and they are used in accordance with the purpose.

Figure 2:
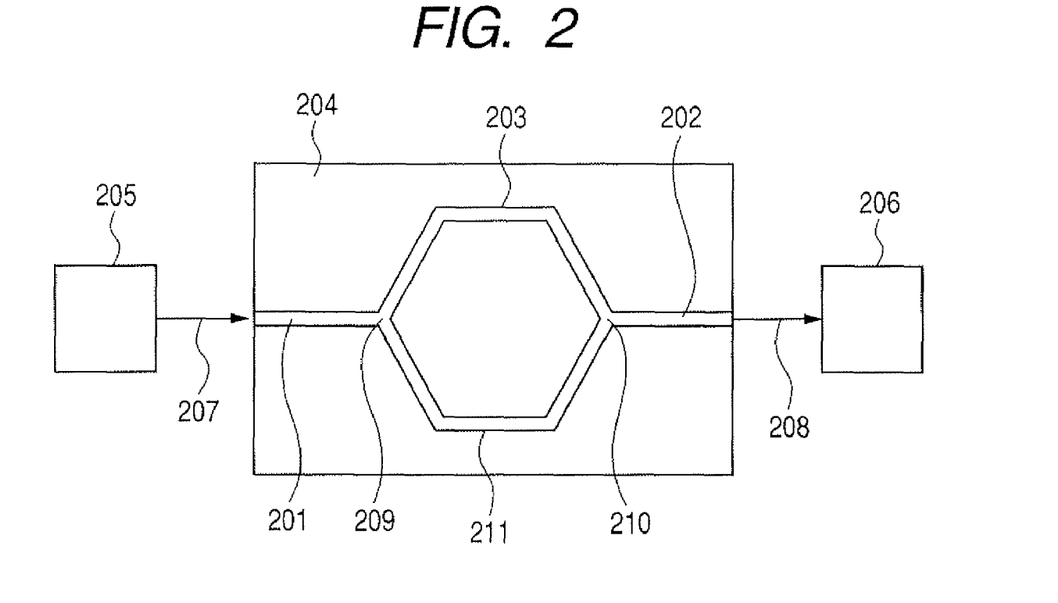
FIG. 2 is a schematic block diagram showing one example of a Mach-Zehnder interferometer.

FIG. 2 shows a schematic block diagram of a Mach-Zehnder interferometer constituted by a Y-branched waveguide formed on a substrate 204. Light 207 emitted from a light source 205 propagates through an optical waveguide 201, and is divided into two light waves at the first Y-branched waveguide 209. The two light waves respectively propagate through the optical waveguide 203 and the optical waveguide 211, and are synthesized into one at the second Y-branched waveguide 210. The synthesized light propagates through the optical waveguide 202, and is emitted from the optical waveguide 202 as light 208. The complex amplitude information of the light 208 is detected in a photo-detecting section 206. If an optical power meter is employed for the photo-detecting section, the intensity of the synthesized light (the intensity of interference light) can be measured with it.

Figure 3:
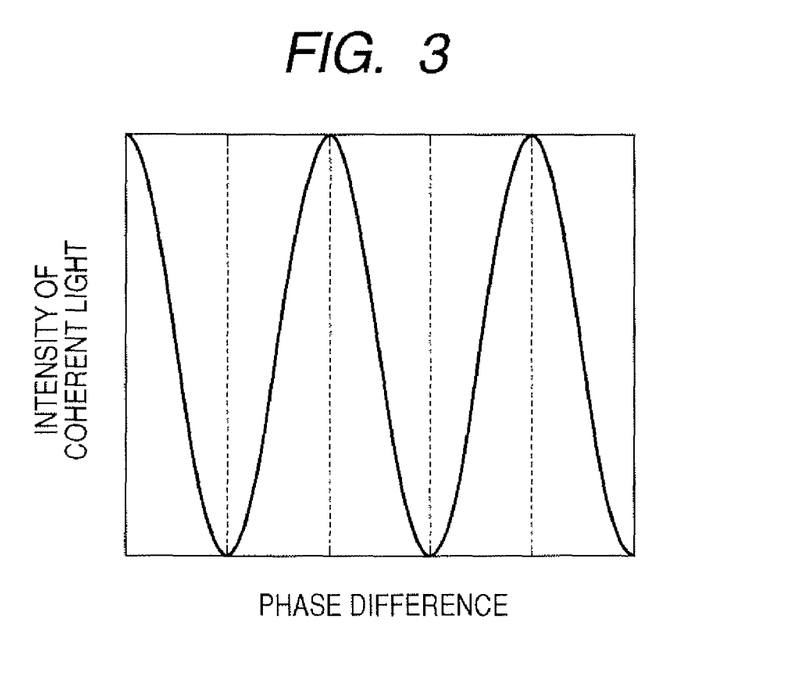
FIG. 3 is a schematic block diagram showing one example of a relationship between a phase difference and the intensity of interference light, when two light waves have been synthesized.

FIG. 3 shows one example of a relationship between a phase difference $\Delta\psi$ between two light waves and the intensity I of interference light, when two light waves having the same angular frequency are synthesized. When each of the two light waves is assumed to have the complex amplitude of $A_1 \cos(\psi_1 - \omega t)$ and the complex amplitude of $A_2 \cos(\psi_2 - \omega t)$, I equals $(A_1 + A_2)^2$ when the phase difference $\Delta\psi$ is even-numbered times of $\pi$, which is the maximum intensity. On the other hand, when the phase difference $\Delta\psi$ is odd-numbered times of $\pi$, I equals $(A_1 - A_2)^2$, which is the minimized intensity.

When the optical path lengths of optical waveguides 203 and 211 are equal, a phase difference becomes 0 and the intensity of interference light is maximized. When an environment in any one of the optical waveguides 203 and 211 changes, and consequently the optical path length changes, the lights having propagated through the optical waveguide 203 and the optical waveguide 211 cause the difference of the phases between them. As a result, the intensity 208 of the interference light changes. By deciding the maximum intensity of the interference light as a reference value and measuring a change in the intensity from the maximum intensity, an amount of change in the environment having occurred in any one of the optical waveguides 203 and 211 can be estimated.

Japanese Patent Application Laid-Open No. 2003-075447 proposes a method for measuring a change of a resonance mode of the photoexcited surface plasmon on a metallic surface with detected light, which is formed due to the coupling of antigen with antibody when the metal surface having the antibody carried thereon contacts with a solution containing the antigen.

A sensor device disclosed in Applied Physics Letters, Vol. 82, No. 26, 30 Jun. 2003, pp. 4648-4650 has a structure of introducing several types of liquids into a micro resonator laser prepared by using a photonic crystal, and measuring the shift of the wavelength of an emitted laser occurring due to a difference of refractive indexes.

When a state of a photonic crystal changes, for instance, a refractive index of a substance constituting the periodic structure of the photonic crystal, or an adsorbed state of another substance to the structure changes, the optical characteristics of the photonic crystal such as a transmission spectrum change. Accordingly, by detecting a change in the optical characteristic of the photonic crystal corresponding with a change in physical quantity such as the concentration of a specified substance in the sample to be detected, the information on the change in the physical quantity of a sample to be detected can be obtained.

Figure 9:
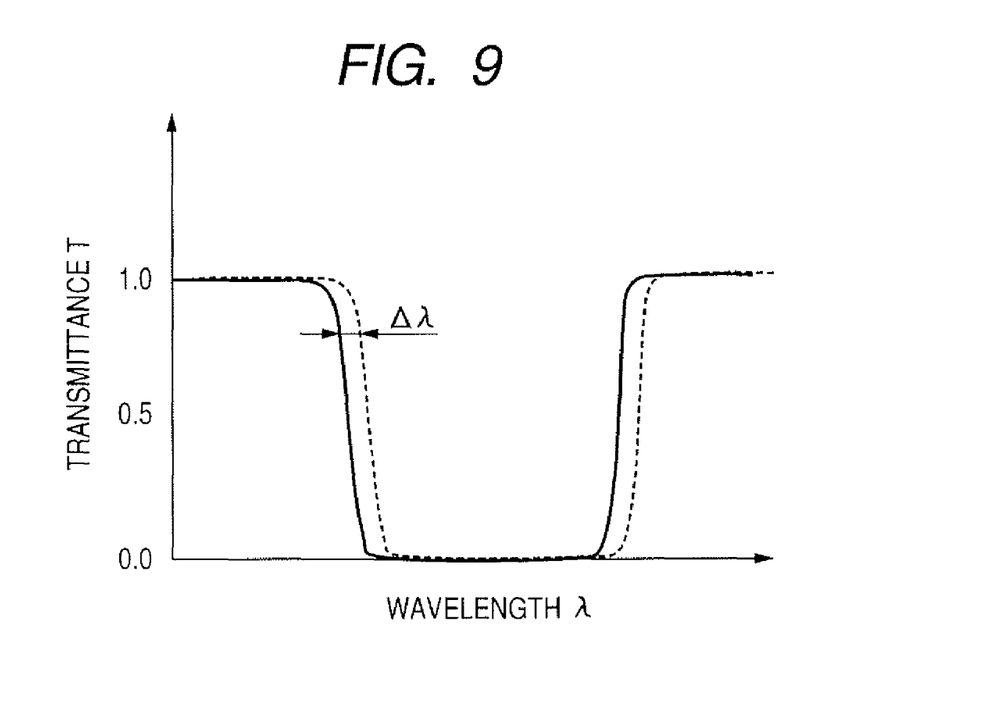
FIG. 9 is a schematic block diagram showing a shift of a transmission spectrum.

When the optical characteristics of the photonic crystal change, incident light onto the photonic crystal is modulated. The modulation includes, for instance, the increase and decrease of the intensity of light, and changes in the phase and the spectral shape of the light. The form of light emitting from the crystal includes transmitted light, luminescent light and reflected light. FIG. 9 diagrammatically shows the state in which a wavelength λ of the light having transmitted through the photonic crystal shifts by Δλ in a spectrum, due to the change of the refractive index of an analyte. Generally, when the refractive index of the photonic crystal increases, the transmission spectrum shifts to a longer side of wavelength. If a quantitative relationship would exist between the amount of the change in the refractive index and the shifted amount of the wavelength, the refractive index can be measured by measuring the transmission spectrum.

Figure 1A:
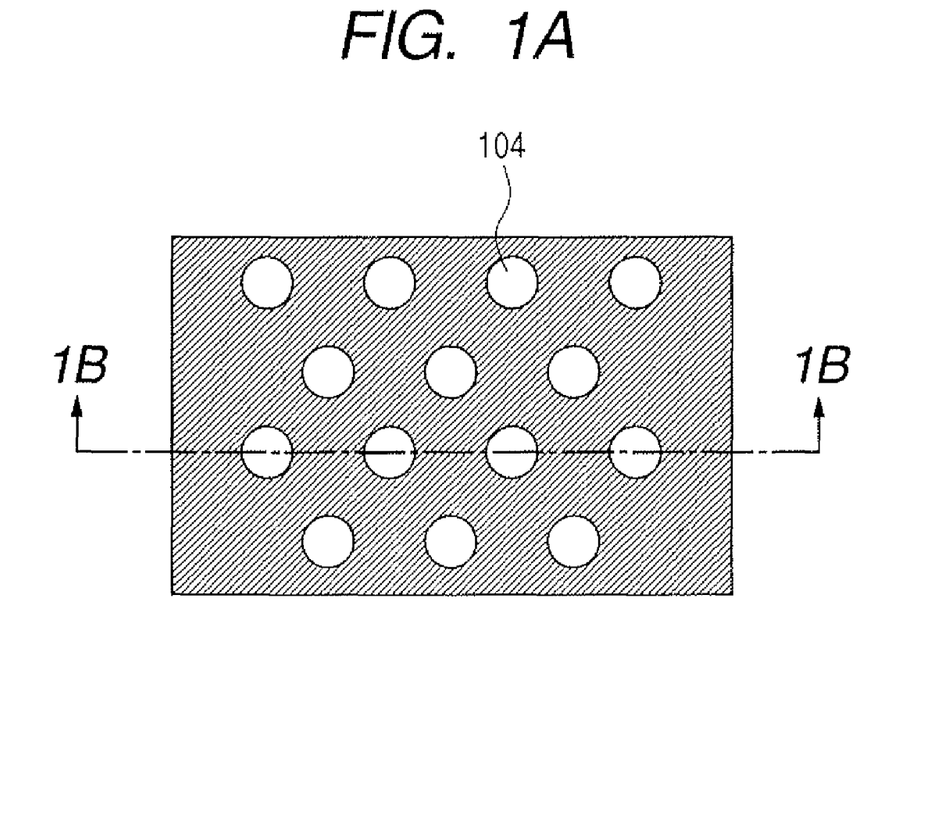
FIGS. 1A and 1B are schematic block diagrams showing one example of a two-dimensional slab photonic crystal produced on a SOI substrate.
Figure 1B:
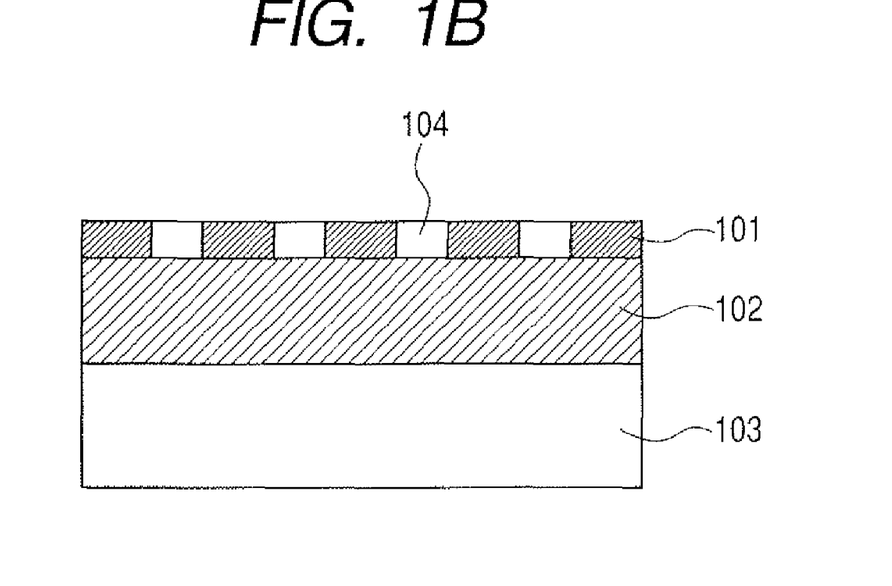

A Si (silicon)-two-dimensional photonic crystal can be prepared relatively easily by applying a semiconductor microprocessing technology. FIGS. 1A and 1B show one example of the Si-two-dimensional photonic crystal prepared on a SOI (Silicon On Insulator) substrate. FIG. 1A is a plan view, and FIG. 1B is a sectional view taken in a median line indicated by 1B-1B on FIG. 1A. The Si-two-dimensional photonic crystal has a $SiO_2$ layer 102 formed on a Si substrate 103; a Si layer 101 further formed thereon; and holes 104 hexagonally symmetrically arranged in the Si layer 101. The Si-two-dimensional photonic crystal has a planar shape, is prepared in a plane process, has a micro size, and accordingly is relatively easily merged with a μ-TAS (also called Micro Total Analysis System or Lab on Chip). By the same token, it is easy to form an optical waveguide in a μ-TAS. Accordingly, in an organism-analyzing/detecting method using the μ-TAS, several Si-two-dimensional photonic crystals and several optical waveguides can be used.

However, a conventional sensor device using a photonic crystal has high sensitivity, and accordingly unavoidably sensitively responds to various environmental changes. As a result, the conventional sensor device has had a problem that a signal-to-noise ratio is decreased when there is a signal to be unexpectedly detected, which is not the signal based on the change to be detected and is so-called disturbance. The disturbance is caused by a change of a refractive index occurring due to a temperature change, deformation in the photonic crystal due to an external force and thermal expansion, vibration and the fluctuation of the density of a buffer solution.

For example, disturbance due to a temperature change will be now described. When the temperature of a photonic crystal rises, the shape of the photonic crystal also changes due to thermal expansion, and simultaneously the refractive index changes. The two effects conspire to shift the wavelength of a transmission spectrum to a longer side, along with the increase of the temperature. When expressing an amount of the shift with $Δλ_2$, the total amount of the shift of the transmission spectrum is expressed by $Δλ=Δλ_1+Δλ_2$. It is difficult to detect only the shifted amount $Δλ_1$ caused by a change in a refractive index, by extracting it from the total amount, and as a result, the shifted amount $Δλ_2$ lowers the sensitivity of the sensor.

SUMMARY OF THE INVENTION

The present invention is directed at providing a sensor device which hardly receives the influence of disturbance.

According to an aspect of the present invention, there is provided a sensor device for detecting a substance contained in a fluid comprising:

a first photonic crystal region, a second photonic crystal region, a first channel which is connected to the first photonic crystal region, and passes the fluid containing the substance therein, a second channel which is connected to the second photonic crystal region, and passes a fluid for reference therein, an optical waveguide which is connected to the first photonic crystal region and the second photonic crystal region, and guides light, and a detecting section for detecting a difference between a light which has passed through the optical waveguide and the first photonic crystal region and a light which has passed through the optical waveguide and the second photonic crystal region.

The sensor device preferably further comprises a light source for emitting light to be incident on the optical waveguide. The optical waveguide preferably includes a branching part for diverging light and introducing each of the diverged lights into the first photonic crystal region and the second photonic crystal region.

The optical waveguide preferably includes a first optical waveguide and a second optical waveguide for guiding light respectively to the first photonic crystal region and the second photonic crystal region. The first optical waveguide preferably has a phase-modulating element installed therein.

The optical waveguide preferably includes a combining part for combining lights each having passed through the first photonic crystal region and the second photonic crystal region.

The structure of a sensor device according to the present invention can realize the sensor device which hardly receives the influence of disturbance. Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

A sensor device according to the present invention is the sensor device for analyzing a type of a fluid of a gas or a liquid in itself, or a target substance contained in the fluid through a mixed or dissolved form, or for detecting a physical quantity such as concentration. A sensor device applicable to the present invention includes, for instance, various interference type sensor devices.

A sensor device according to the present invention is constituted by a light source, an optical waveguide, a plurality of photonic crystals, a plurality of channels for passing a sample fluid to be detected and a reference fluid, and a photo-detecting section. A plurality of the channels are each connected with a plurality of the photonic crystals in one part of the area. The optical waveguide guides a light with a wavelength in a predetermined range emitted from the light source to both of the photonic crystals, and guides the light emitted from the photonic crystal to the photo-detecting section. The photo-detecting section detects the complex amplitude information of several emitted lights.

In the present invention, "the connection between a channel and a photonic crystal" means the state in which both of the channel and the photonic crystal are arranged so that a sample fluid to be detected flowing through the channel can affect the optical characteristic of the photonic crystal. Accordingly, "the connection between a channel and a photonic crystal" includes the state in which the photonic crystal is arranged in the channel, and the state in which the photonic crystal is arranged around the channel so that the fluid can flow into the photonic crystal from the channel.

A position in which a photonic crystal is arranged in the present invention is in an optical waveguide or even in the vicinity thereof. Here, the vicinity means a range in which a photoelectric magnetic field is affected. The range depends on a wavelength of light, but is approximately in a wavelength order. For instance, when the wavelength of light is 1.5 µm, the range is about 0.5 to 10 µm.

A structure of a photonic crystal is not particularly limited, as long as it can be connected to a channel. A binding substance to be selectively coupled with a specified substance may be carried on the surface of the photonic crystal.

At least one photonic crystal out of a plurality of photonic crystals is used for reference. Hereafter, such a photonic crystal as the characteristics are affected by contacting with a sample fluid to be detected is called "a photonic crystal for detection" or "a first photonic crystal", and a photonic crystal used for reference is called "a photonic crystal for reference" or "a second photonic crystal". The first photonic crystal for detection and the second photonic crystal for reference may have different structures, but preferably have the same structure so as to make the first and second photonic crystals have equal effects of disturbance. It is also acceptable to use both of the photonic crystals while interchanging the purposes from detection to reference and vice versa.

Here, a principle of reducing disturbance by using a plurality of photonic crystals will be described.

The method employs, for instance, one first photonic crystal out of two photonic crystals of the first and second photonic crystals having the same structure, for detection, and the other second photonic crystal for reference. Assume to have introduced a fluid for detection (for instance, a mixture of a buffering solution and protein) into the first photonic crystal for detection, and a fluid for reference (for instance, a simple buffer solution) to the second photonic crystal for reference. If the two photonic crystals would receive common influence by the disturbance, a difference between them is only the presence or absence of protein. Here, it can be said that a difference between transmission spectrums from the two photonic crystals is caused only by the presence or absence of the protein, so that the photonic crystals can detect a value from which the influence of the disturbance has been canceled.

In the above described example, description was made on the case of measuring the shift of a transmission spectrum for the sake of simplicity, but the same principle can be applied to the case of measuring another optical property (such as changes of intensity and a phase). An important thing is that a value having the influence of disturbance reduced therein can be detected by measuring a difference between a plurality of photonic crystals.

First and second channels are formed of a flute or a hole on the surface or the inside of a substrate, and have a structure capable of passing a separate fluid into each of first and second photonic crystals. A material for forming the channel has only to be resistant to a fluid, but specifically includes polymethylmethacrylate (PMMA), polydimethylsiloxane (PDMS) and glass. A size of each channel is not particularly limited as long as the channel can be connected with a photonic crystal, but when considering a fluid control technology using a laminar flow used in µ-TAS and the like, the size is preferably about 1 to several hundreds of micrometers in width. Each channel preferable has the same structure, size and the like.

An optical waveguide has a structure capable of guiding light to each of the first and second photonic crystals, and guiding the light emitted from a plurality of the photonic crystals to a photo-detecting section. Accordingly, the optical waveguide may be composed of a group of several independent optical waveguides corresponding to each of photonic crystals, or may be a single optical waveguide as a whole, which is diverged to each photonic crystal at midstream.

A photo-detecting section has means for detecting a difference between the complex amplitude information of emitted lights, which is caused by a difference between optical characteristics of a photonic crystal for detection and a photonic crystal for reference. The means includes, for instance, means for measuring the intensity of each transmitted light with a detecting device to electrically process the signal, and means for measuring the intensity of the interference light which synthesized from transmitted lights.

A specific example of a sensor device according to the present invention will be described with reference to FIG. 4.

Pass a fluid for detection to a first channel 410 connected to a first photonic crystal 403, and a fluid for reference to a second channel 411 connected to a second photonic crystal 404. Light 408 is emitted from one light source 405, is temporarily guided to a common wave guide 401, is diverged at a Y-branch 412, and is then guided to each of the photonic crystals 403 and 404. The lights having passed through each of the photonic crystal and emitted therefrom are respectively guided to the wave guides 414 and 415, are again optically coupled at a Y-branched waveguide 413, passes through a wave guide 402 as light 409, and is input to a photo-detecting section 406.

It is also acceptable to use two light sources and guide each light emitted from each light source to the photonic crystal.

It is also acceptable to combine the lights having passed through each photonic crystal and having been emitted therefrom in the photo-detecting section, instead of combining them in an optical waveguide.

A first channel 403 and a second channel 411 are not necessarily separated from each other from beginning to end, but have only to be diverged at the upstream of the photonic crystals.

Figure 4:
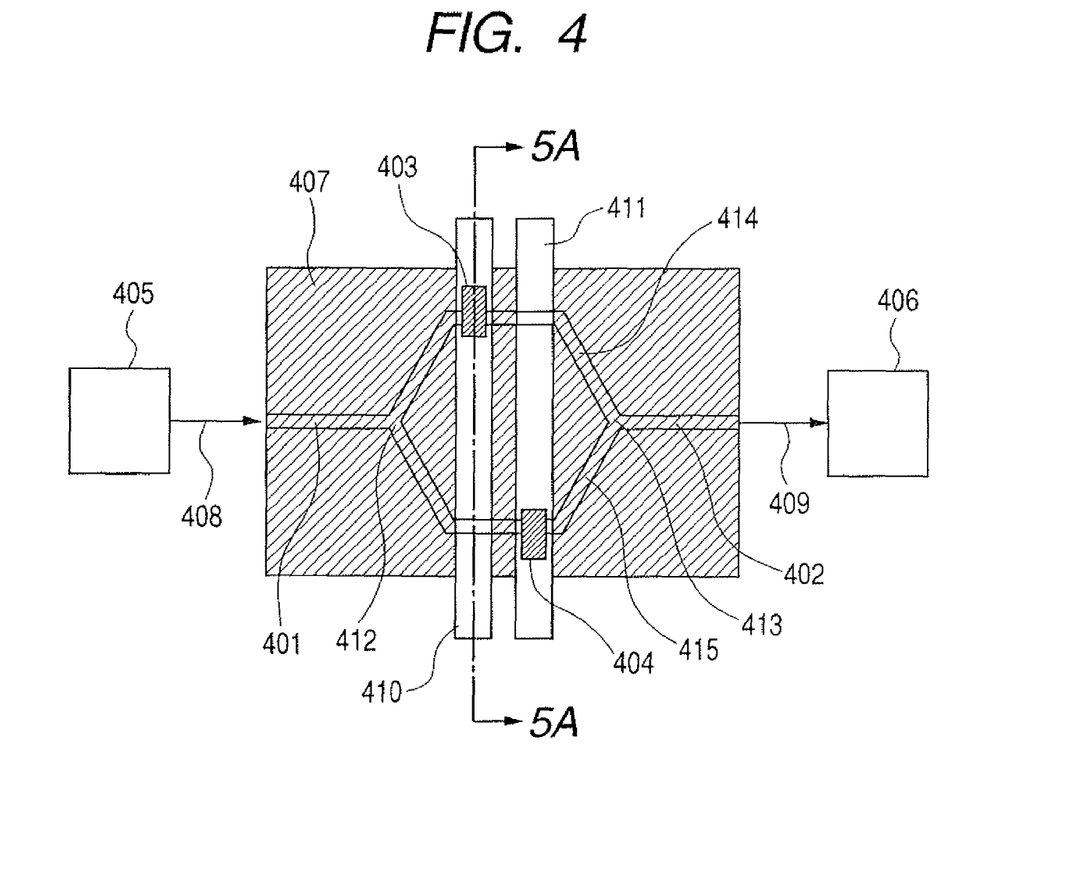
FIG. 4 is a schematic block diagram showing a structure of a sensor device in Embodiment 1 using the Mach-Zehnder interferometer.

As is shown in FIG. 4, a sensor device according to the present invention does not reduce disturbance in itself, but employs a method of canceling the influence of the disturbance, by using a plurality of photonic crystals and measuring a difference among the values from them.

An example of a gaseous fluid to be detected by a sensor device according to the present invention includes the followings: a gas sensor for detecting an exhaust gas from an internal combustion engine ($O_2$, CO, NO, $NO_2$, $SO_2$, CO and the like); a gas sensor mounted on a security alarm for a combustible gas such as carbon monoxide (methane, propane, butane and the like), which is used in an ordinary household; a gas sensor for detecting an organic gas component (ethanol, acetaldehyde, ammonia, acetic acid and the like) included in an expired gas; a sensor for detecting such a substance as to deteriorate a work environment in a factory or an office ((particulate (dust), free silicic acid, sulphur oxide ($SO_x$), nitrogen oxide ($NO_x$), cadmium, chlorine, hydrogen chloride, fluorine, lead, phenol, antimony, benzene, trichloroethylene, tetrachloroethylene, dioxins, coplanar PCB, mercury, formaldehyde, toluene, xylene, styrene monomer, paradichlorobenzene, acrylonitrile, acetaldehyde, vinyl chloride monomer, chloroform, ethylene oxide, 1,2-dichloroethane, dichloromethane, mercury, dioxins, talc, tetrachloroethylene, trichloroethylene, a nickel compound, arsenic, 1,3-butadiene, floating dust, beryllium, benz(a)pyrene, benzene, formaldehyde, manganese, chromium, ammonia, methyl mercaptan, hydrogen sulfide, methyl sulfide, methyl disulfide, trimethylamine, acetaldehyde, propionaldehyde, normal butylaldehyde, isobutylaldehyde, normal valeraldehyde, isovaleraldehyde, isobutanol, ethylacetate, methyl isobutyl ketone, toluene, styrene, xylene, propionic acid, normal butyric acid, normal valeric acid and isovaleric acid); and a sensor for detecting a volatile environmental pollutant and a substance causing global warming (chloroform, carbon tetrachloride, trichloroethylene, 1-1-1 trichloroethane, tetrachloroethylene, flon and the like).

An example of a sensor device according to the present invention for detecting a liquid fluid roughly classified into the followings:

(1) a sensor device for an environmental pollutant;

(2) a sensor device for controlling a process and quality in industry such as the chemical industry, the food-stuff industry and the pharmaceutical industry, and for combinatorial synthesis and combinatorial screening; and (3) a sensor device for diagnosing disease and health status.

(1) A form of a sensor device according to the present invention to be used as a sensor device for an environmental pollutant includes: a sensor device for analyzing a quality of water in river, lake and sea (cadmium, a cyanogen compound, organic phosphorous compound, lead, hexavalent chromium, arsenic, total mercury, alkyl mercury, PCB, trichloroethylene, tetrachloroethylene, dichloromethane, carbon tetrachloride, 1,2-dichloroethane, 1,1-dichloroethylene, cis-1,2-dichloroethylene, 1,1,1-trichloroethane, 1,1,2-trichloroethane, 1,3-dichloropropene, thiuram, simazine, thiobencarb, benzene, selenium and the like); a sensor device for analyzing agricultural chemicals in agriculture and forestry drainage (isoprothiolane, iprodione, etridiazole, oxine-copper (organocopper), captan, chlorothalonil, chloroneb, acephate, isoxathion, diazinon, pyridaphenthion, fenitrothion (MEP), asulam, napropamide, butamifos, bensulide (SAP) and mecoprop); and a sensor for analyzing environmental endocrine disrupter (4-octylphenol, nonylphenol, di(2-ethylhexyl)phthalate, butylbenzyl phthalate, di-n-butyl phthalate, dicyclohexyl phthalate, diethyl phthalate, di(2-ethylhexyl)adipate, bisphenol A, styrene monomer, dioxins, polychlorinated biphenyl (PCB), polybromide biphenyl (PBB), hexachlorobenzene (HCB), pentachlorophenol (PCP), 2,4,5-trichlorophenoxyacetic acid, 2,4-dichlorophenoxyacetic acid, amitrole, atrazine, alachlor, hexachlorocyclohexane, chlordane and oxychlordane).

In addition, the sensor device according to the present invention can detect an environmental pollutant in soil and solid waste as a target substance, by using a liquid fluid as a sample, which has been prepared by extracting the above described environmental pollutant from the soil or the solid waste with a liquid medium, or further removing a solid component with a filter in some cases.

(2) A form of a sensor device according to the present invention to be used as a sensor device in industry such as the chemical industry, the food-stuff industry and the pharmaceutical industry includes: a food sensor device for allergen check of an ingredient, factory-shipped safety test (food poisoning microorganism and toxin) and the like; and a combinatorial synthesis/combinatorial screening sensor device for selecting a desired substance from a large amount of library candidate substances or combination synthesis reactions, in the chemical industry and the pharmaceutical industry.

Particularly, in a field of drug development in the pharmaceutical industry, an interaction between protein and peptide, an interaction between gene and protein such as a transcription factor, and the like have been elucidated in recent years, and they have begun to be applied to a protein preparation and a genetic preparation. The sensor device according to the present invention can screen a target substance having a useful pharmacologic action, by immobilizing specific DNA, protein or peptide on a solid part of the sensor device as a binding substance, and detecting DNA, protein, peptide or a chemical synthesis compound of a target substance to be specifically coupled with the above described binding substance, out of a large amount of a library substances.

(3) A form of a sensor device according to the present invention to be used as a sensor device for diagnosing disease and health status includes a sensor device for detecting protein, glycoprotein, lipoprotein, peptide or the complex thereof, which are called a disease marker and contained in a body fluid of a subject such as blood, urine, saliva and lymph, as a target substance, or in a solution liquid-extracted from a lesion cell of the subject, by immobilizing an antibody specific to them as a binding substance on the surface of a hole image side of a solid part in the sensor device according to the present invention, introducing the above described target substance to the sensor device through a channel, and progressing a specific coupling reaction thereon. In this case, when a blood cell component in blood and a coloring component in another body fluid disturb detection, they are preferably removed with a filter previously.

A preferred embodiment of a sensor device according to the present invention will be now shown below.

The above described physical quantity is preferably a refractive index of a fluid.

The above described physical quantity is preferably a concentration of a substance included in the fluid.

The surface of the above described photonic crystal has preferably a binding substance carried thereon, which is selectively coupled with a specified substance.

The above described complex amplitude information of the light emitted from the photonic crystal preferably changes along with the change of the above described physical quantity.

The above described change of the complex amplitude information is preferably a phase change.

The above described change of the complex amplitude information is preferably the change of amplitude.

It is preferable to detect a difference of the above described complex amplitude information, by detecting the intensity with the use of a Mach-Zehnder interferometer.

The sensor device has preferably a phase-modulating element for changing a phase of irradiating light or emitted light by a predetermined quantity, arranged in one part of the above described optical waveguide.

It is preferable to detect the difference of the above described complex amplitude information with a synchronous detection system.

The sensor device has preferably an element having a groove or a hole as the above described channel arranged on a plane containing the above described photonic crystal.

EMBODIMENTS

In the next place, the present invention will be further specifically described with reference to embodiments.

Embodiment 1

A sensor device in the present embodiment employs a Mach-Zehnder interferometer, and has a photonic crystal and a channel according to the present invention therein. The structure of the present embodiment will be now described with reference to FIG. 4 and FIGS. 5A to 5C.

Figure 5A:
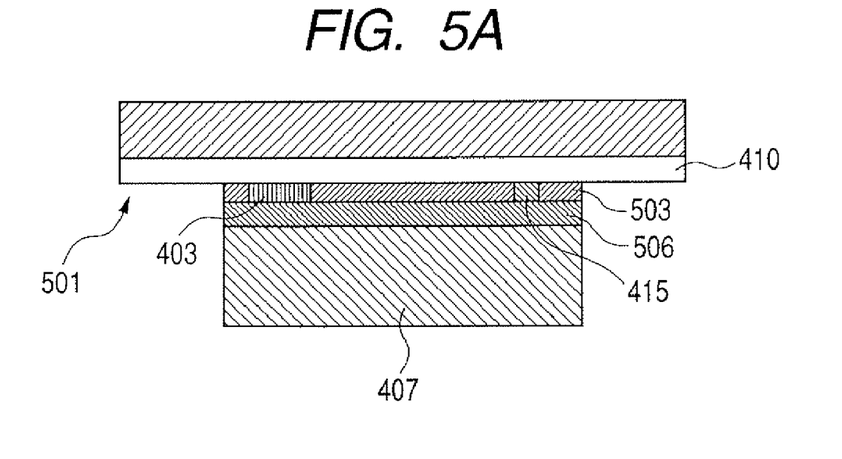
FIG. 5A is a schematic block diagram showing the section taken in a line 5A-5A in FIG. 4.

The sensor device has two photonic crystals 403 and 404 arranged on a Mach-Zehnder interferometer composed of a substrate 407, a $SiO_2$ layer 506 and a Si layer 503. Light 408 emitted from a light source 405 into an optical waveguide 401 is divided into two light waves at the first Y-branched waveguide 412, and each of the divided lights passes through a first photonic crystal 403 and an optical waveguide 414, and through a second photonic crystal 404 and an optical waveguide 415. Afterwards, they are synthesized to one at the second Y-branched waveguide 413, and the intensity of the light 409 emitted from the optical waveguide 402 is detected by a photo-detecting section 406. Specifically, each photonic crystal is separately connected to each optical waveguide, and is arranged in parallel to each other.

Figure 5B:
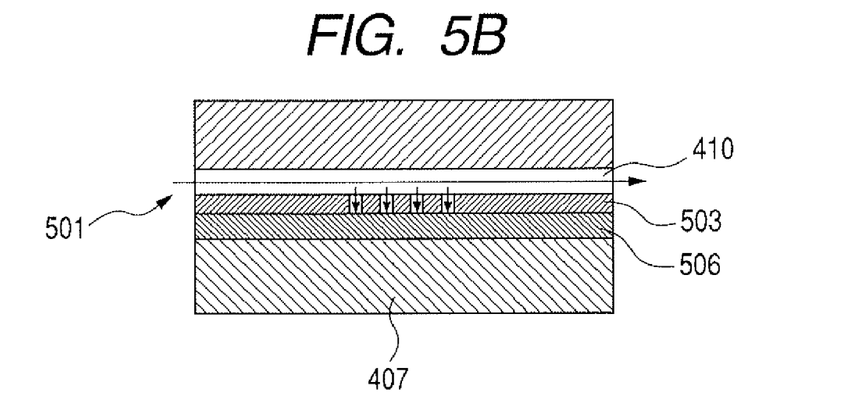
FIGS. 5B and 5C are views expanding one part of FIG. 5A.
Figure 5C:
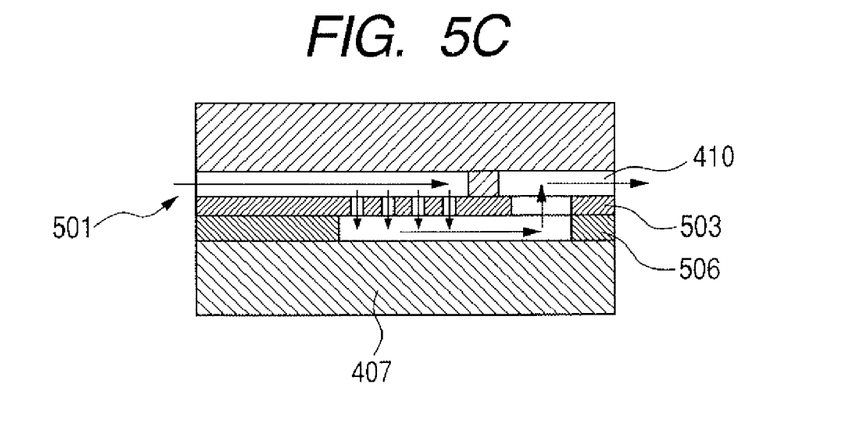

FIG. 5A shows a view of a section cut along a line 5A-5A shown in FIG. 4, and FIGS. 5B and 5C show a schematic block diagram which expands a photonic crystal 403 and the vicinity thereof shown in FIG. 5A. A channel chip 501 has a groove 410 formed therein, and forms a channel when having been arranged on a Si layer 503. The channel can have several shapes. The channel can have the shape of passing a fluid along the surface of a photonic crystal as shown in FIG. 5B, and the structure which prepares the groove in upper and lower parts of the photonic crystal and passes the fluid through a hole in the photonic crystal, as shown in FIG. 5C.

In the present embodiment, the sensor device detects a phase difference between lights which have passed through different photonic crystals. In the next place, the principle will be described.

Considering the case of using a photonic crystal 403 for detection and a photonic crystal 404 for reference. If an optical waveguide 414 including the photonic crystal 403 for detection and an optical waveguide 415 including the photonic crystal 404 for reference would have equal optical path lengths, the two lights have no phase difference between them and the intensity of the interference light is maximized. Here, pass a fluid to be detected to the photonic crystal for detection and a fluid for reference to the photonic crystal for reference through each of the channels 410 and 411, and the two lights having passed through the photonic crystal for detection and the photonic crystal for reference forms the difference between their phases due to the difference between physical quantities of the fluids. As a result of this, the intensity of interference light 409 changes. Then, it becomes possible to estimate the difference between the physical quantities of the fluid for detection and the fluid for reference, by setting the maximum value of the interference light intensity as a reference value, and measuring a change of the intensity from the reference value with a photo-detecting section 406.

An effect of forming a Mach-Zehnder interferometer instead of separately measuring a transmitted light from each of photonic crystals and determining the difference includes that the sensor device can be inexpensively prepared and miniaturized, because the number of light sources, photo-detecting sections and electric circuits are reduced.

Figure 6:
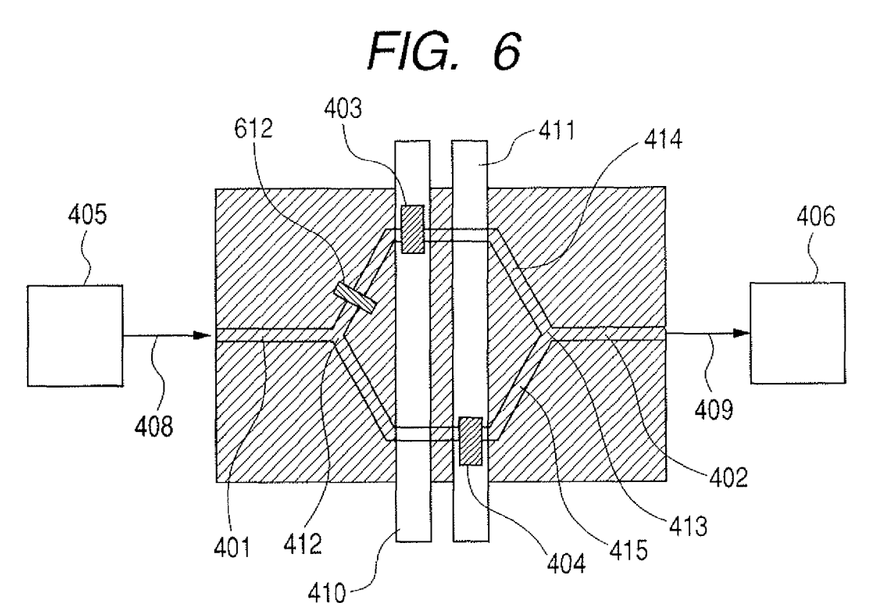
FIG. 6 is a schematic block diagram showing another structure of the sensor device in Embodiment 1 using a Mach-Zehnder interferometer.

It is also permitted, as shown in FIG. 6, to form a structure of arranging a phase-modulating element 612 having a function of changing a phase of light by a predetermined quantity, on any one of branched waveguides. Arrange the phase-modulating element for shifting the phase of the light by Π for instance, and the sensor device can set the above described reference value to the minimum intensity of interference light. Not only the minimum intensity, but also arbitrary intensity can be set to the reference value by controlling the phase shift. The phase-modulating element may modulate the light incident on a photonic crystal, or may modulate an emitted light therefrom.

If the sensor device would be provided with a thermostat for preventing the influence of disturbance, the sensor device would be upsized and/or need a high cost. However, a structure shown in the present embodiment though being simple can cancel the disturbance.

Embodiment 2

The present embodiment shows one form of detecting synchronous light, while using a sensor device according to the present invention and a lock-in amplifier. A structure of the sensor device in the present embodiment will be now described with reference to FIG. 7.

Figure 7:
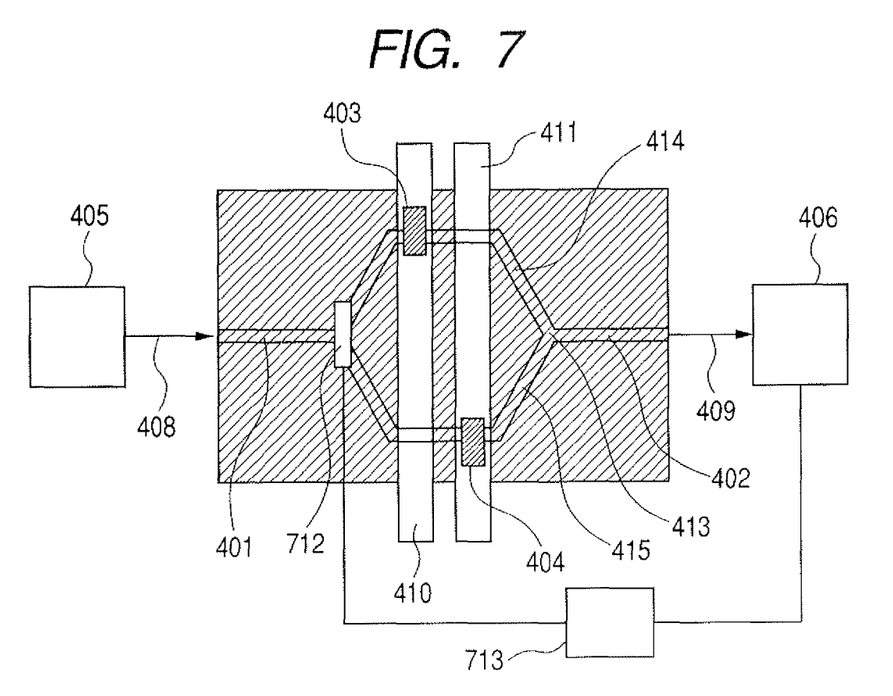
FIG. 7 is a schematic block diagram showing the structure of the sensor device in Embodiment 2 using a synchronous detection system.

A structure of the present embodiment employs a Mach-Zehnder interferometer similarly to the structure in Embodiment 1, but uses a synchronous detection system instead of measuring the intensity of interference light for a method for detecting the difference, which is a point different from the structure in Embodiment 1. The synchronous detection system is a procedure often used for removing noise. The sensor device has an optical switch 712 arranged in the first Y-branching part; makes the optical switch modulate incident light 408; synthesizes the lights having passed through photonic crystals 403 and 404 at the second Y-branched waveguide 413; makes a photo-detecting section 406 detect the light 409; and makes the lock-in amplifier 713 detect only a signal synchronizing with the modulated incident light out of detected signals. A light chopper or an MEMS switch can be used for the optical switch.

The structure of the present embodiment shows the effects of: reducing the influence of disturbance according to the same principle as in Embodiment 1; increasing a signal-to-noise ratio because of using a synchronous detection system;

and requiring a few numbers of photo-detecting sections and electric circuits, in contrast to the structure of separately detecting each of lights having passed through each of photonic crystals.

Embodiment 3

The present embodiment shows one form of a sensor device according to the present invention, which detects a refractive index of a fluid. The sensor device according to the present embodiment has the same structure as is shown in Embodiment 1 or 2, and detects the refractive index of the fluid flowing in a channel.

For instance, pass a fluid into a channel in the structure of a sensor device shown in FIG. 4. Specifically, pass the fluid having a refractive index to be detected into a channel 410 and a fluid having a known refractive index into a channel 411, and lights having passed through a photonic crystal 403 and a photonic crystal 404 cause a phase difference between them due to a difference between the refractive indexes of two fluids, and thereby the intensity of interference light changes. Then, when detecting the refractive index, take a procedure of estimating a quantity of a phase change from a quantity of change in the intensity of interference light, and estimating the refractive index of the fluid therefrom.

A prior art has employed a method for detecting a shift of a spectrum of a transmitted light or an emitted light caused by a refractive index of a fluid, in order to detect the refractive index of the fluid with the use of a photonic crystal. The present embodiment includes detecting a change in a phase of a transmitted light caused by a change in the refractive index of the fluid, by using a plurality of the photonic crystals and a Mach-Zehnder interferometer.

When a refractive index of a fluid changes according to the concentration of a substance contained in the fluid, the concentration of the substance can be detected by measuring the refractive index. An example of such a fluid includes a sucrose solution or a glycerol solution.

Embodiment 4

The present embodiment shows one form of a sensor device according to the present invention, which is a biochemical sensor that uses particularly a specific coupling reaction such as an antigen-antibody reaction. The sensor device according to the present embodiment has the same structure as is shown in Embodiment 1 or 2, and detects the concentration of a specified substance in a fluid. A structure of the sensor device in the present embodiment will be now described with reference to FIG. 8.

Figure 8:
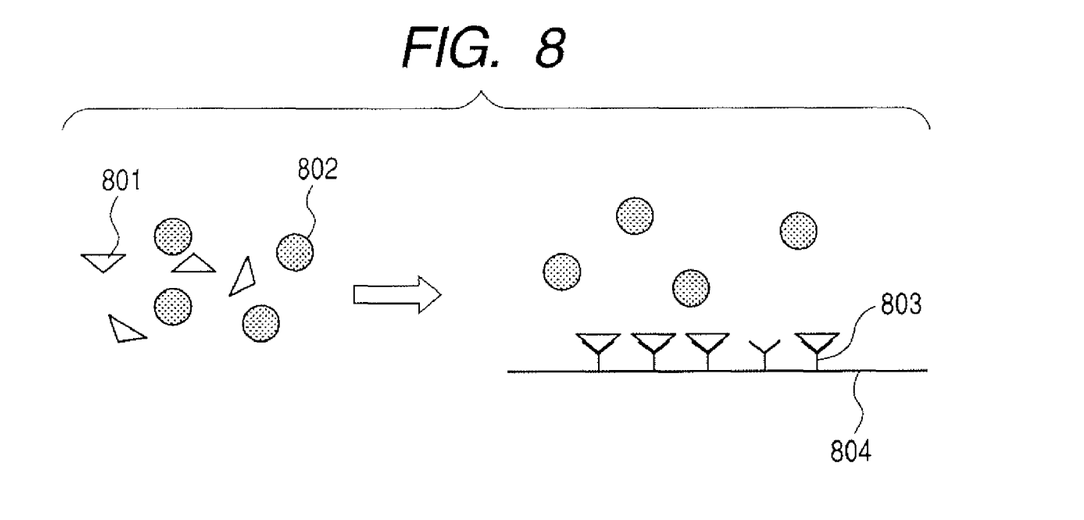
FIG. 8 a schematic block diagram showing the structure of the sensor device in Embodiment 4 using an antigen-antibody reaction.

FIG. 8 is a schematic block diagram showing a state of the surface 804 of a photonic crystal which has carried such a substance (antibody) 803 as to specifically bind to a specific substance (antigen). Here, pass a fluid including the antigen 801, another substance 802 or the like in a sensor device having a structure shown in FIG. 4, and the antibody specifically absorbs the antigen. The optical characteristic of the photonic crystal is changed by the coupling of the antibody with the antigen. The change can be explained to be caused by a change of a dielectric constant and refractive index of the surface of the photonic crystal due to the change of an electronic state of the surface of the photonic crystal, or simply by a change of the refractive index of the photonic crystal. Whatever the cause is, it is an essential point in the present embodiment that optical characteristics of the photonic crystal change due to the coupling, and the sensor device can estimate an amount of adsorbed substance to the surface of the photonic crystal by detecting the amount of the change.

In addition to the photonic crystal with the structure shown in FIG. 1, a similar structure of a sensor device is also permitted as a matter of course, which employs a photonic crystal consisting of periodically arranged columns.

The sensor device can also employ the structure in which the positions of an antigen and an antibody are reversed, or equivalently the structure in which the antigen is carried on the surface of the photonic crystal and the antibody is coupled thereto.

The sensor device further can employ a structure of simply using physical adsorption instead of using an antigen-antibody reaction. In this case, it becomes difficult for the sensor device to detect a specified substance by making the photonic crystal selectively adsorb only the specified substance, but the sensor device has an advantage of being prepared in a simpler process. The structure can be used for a fluid containing only one substance, or a fluid in which only the specified substance extremely sufficiently adsorbs to the surface of a photonic crystal even having no antibody carried thereon.

The sensor devices shown in the above described embodiments have a structure of using two channels and two photonic crystals, but can have the structure of using three or more channels and three or more photonic crystals according to a similar principle. For instance, the sensor device can have a plurality of the photonic crystals thereon each of which carries a different antibody from each other, and then the sensor device can detect the concentrations of several types of substances in a fluid, at a time.

In addition, the sensor devices shown in the above described embodiments have a layer structure using silicon (Si) on silicon oxide ($SiO_2$) as materials of a photonic crystal, but can appropriately select the layer structure using materials such as silicon nitride on porous silicon, and Teflon (registered trademark) on mesoporous silica, in accordance with a measurement environment and an application. The present invention is not limited by the material.

INDUSTRIAL APPLICABILITY

A sensor device according to the present invention can be used for a refractive index sensor, a medical sensor and a microchannel reactor.

As many apparently widely different embodiments of the present invention can be made without departing from the spirit and scope thereof, it is to be understood that the invention is not limited to the specific embodiments thereof except as defined in the claims.

This application claims priority from Japanese Patent application No. 2005-051998 filed on Feb. 25, 2005, which is hereby incorporated by reference herein.

What is claimed is:

1. A sensor device for detecting a substance contained in a fluid comprising:
   a first photonic crystal region;
   a second photonic crystal region;
   a first channel which is connected to the first photonic crystal region, and passes the fluid containing the substance therein;
   a second channel which is connected to the second photonic crystal region, and passes a fluid for reference therein;
   an optical waveguide which is connected to the first photonic crystal region and the second photonic crystal region, and guides light; and
   a detecting section for detecting a difference between a light which has passed through the optical waveguide and the first photonic crystal region and a light which has passed through the optical waveguide and the second photonic crystal region,
   wherein the optical waveguide includes a first optical waveguide and a second optical waveguide for guiding light respectively to the first photonic crystal region and the second photonic crystal region, and wherein the first optical waveguide has a phase-modulating element installed therein.

2. The sensor device according to claim 1, further comprising a light source for emitting light to be incident on the optical waveguide.

3. The sensor device according to claim 2, wherein the optical waveguide includes a branching part for diverging light and introducing each of the diverged lights into either the first photonic crystal region or the second photonic crystal region.

4. The sensor device according to claim 1, wherein the optical waveguide includes a combining part for combining lights each having passed through the first photonic crystal region or the second photonic crystal region.

* * * * *